(12) United States Patent
Hwang et al.

(10) Patent No.: US 11,103,196 B2
(45) Date of Patent: Aug. 31, 2021

(54) APPARATUS AND METHOD FOR PREDICTING PHYSICAL STABILITY

(71) Applicant: Daegu Gyeongbuk Institute of Science and Technology, Daegu (KR)

(72) Inventors: Sang Ho Hwang, Gyeongsan-si (KR); Won Seok Kang, Daegu (KR); Sang Hun Yun, Daegu (KR)

(73) Assignee: DAEGU GYEONGBUK INSTITUTE OF SCIENCE AND TECHNOLOGY, Daegu (KR)

( * ) Notice: Subject to any disclaimer, the term of this patent is extended or adjusted under 35 U.S.C. 154(b) by 400 days.

(21) Appl. No.: 16/183,759

(22) Filed: Nov. 8, 2018

(65) Prior Publication Data

US 2019/0142347 A1 May 16, 2019

(30) Foreign Application Priority Data

Nov. 9, 2017 (KR) .......................... 10-2017-0148949

(51) Int. Cl.
*A61B 5/00* (2006.01)
*A61B 5/0205* (2006.01)
(Continued)

(52) U.S. Cl.
CPC ............ *A61B 5/7275* (2013.01); *A61B 5/002* (2013.01); *A61B 5/0205* (2013.01); *A61B 5/1113* (2013.01); *A61B 5/18* (2013.01); *A61B 5/7225* (2013.01); *A61B 5/7267* (2013.01); *G16H 10/60* (2018.01); *G16H 50/20* (2018.01); *G16H 50/30* (2018.01); *G16H 50/70* (2018.01); *A61B 5/02405* (2013.01); *A61B 5/1118* (2013.01);
(Continued)

(58) Field of Classification Search
None
See application file for complete search history.

(56) References Cited

U.S. PATENT DOCUMENTS

2004/0133081 A1* 7/2004 Teller ................... A61B 5/4884
600/300
2014/0073486 A1* 3/2014 Ahmed .............. A61B 5/02438
482/9

FOREIGN PATENT DOCUMENTS

JP 2008-292294 12/2008
JP 2013-223671 10/2013
(Continued)

OTHER PUBLICATIONS

Han et al. "Active Selection of Label Data for Semi-Supervised Learning Algorithm", Journal of IKEEE, 17(3): 254-259, Sep. 2013. English Abstract.

*Primary Examiner* — Michael W Kahelin
(74) *Attorney, Agent, or Firm* — Lex IP Meister, PLLC (57) ABSTRACT

A physical stability determination system includes a wearable device configured to collect sleep information, activity information and heartbeat information of a user, a data preprocessor configured to divide each of the activity information and the heartbeat information into data of a sleep area and data of an activity area, based on the sleep information, and a data processor configured to calculate a sleep state, an activity intensity or a heartbeat state of the user from the data of the sleep area and the data of the activity area. The data of the sleep area may be used to calculate the sleep state in the data processor, and the data of the activity area may be used to calculate the activity intensity or the heartbeat state in the data processor.

10 Claims, 6 Drawing Sheets

(51) Int. Cl.
*G16H 10/60* (2018.01)
*G16H 50/20* (2018.01)
*A61B 5/11* (2006.01)
*G16H 50/30* (2018.01)
*G16H 50/70* (2018.01)
*A61B 5/18* (2006.01)
*A61B 5/024* (2006.01)

(52) U.S. Cl.
CPC ........... *A61B 5/4812* (2013.01); *A61B 5/4815* (2013.01); *A61B 2503/20* (2013.01)

(56) References Cited

FOREIGN PATENT DOCUMENTS

| | | |
|---|---|---|
| KR | 101306528 | 9/2013 |
| WO | WO 2016/075175 | 5/2016 |

* cited by examiner

APPARATUS AND METHOD FOR PREDICTING PHYSICAL STABILITY

FIELD AND BACKGROUND OF THE INVENTION

Example embodiments relate to a physical stability determination system and method, and more particularly, to a physical stability determination system and method that may determine a degree of a physical stability of a user (for example, a worker or laborer) based on sleep information, activity information, or heartbeat information.

In a work environment where dangerous factors are involved, a physical stability of a worker is most important. A decrease in concentration due to a reduction in a physical stability may lead to loss of life and property damage. However, a physical stability of a worker in the industrial field has been determined only by a subjective judgment of a manager or a co-worker until now, and an accuracy of such a visual determination decreases.

For example, KR 10-2011-0120261 discloses "predictive systems for body activities and overall stress index."

SUMMARY OF THE INVENTION

Example embodiments provide a physical stability determination system and method that may determine a degree of a physical stability of a worker or laborer based on a variety of information, for example, a sleep state of the previous day, a current activity state, a resting heart rate, and the like.

Example embodiments provide a physical stability determination system and method that may prevent loss of life and property damage due to a decrease in concentration by determining a level of difficulty of a job currently available to a worker based on a determined degree of a physical stability.

Example embodiments provide a physical stability determination system and method that may increase a reliability of a physical stability rating through semi-supervised learning when time series data collected by a wearable device is preprocessed and processing by an equation is performed.

Example embodiments provide a physical stability determination system and method that may be effectively utilized in a high-risk work situation, in particular, an occupational group that is forced to continuously work at the beginning of a work by determining a state of a worker before a work, and that may predict whether a worker or trainee (who may be applicable to a variety of fields) maintains a physical stability suitable for a work, before the work is performed.

According to an aspect, there is provided a physical stability determination system including a wearable device configured to collect sleep information, activity information and heartbeat information of a user, a data preprocessor configured to divide each of the activity information and the heartbeat information into data of a sleep area and data of an activity area, based on the sleep information, and a data processor configured to calculate a sleep state, an activity intensity or a heartbeat state of the user from the data of the sleep area and the data of the activity area, wherein the data of the sleep area is used to calculate the sleep state in the data processor, and the data of the activity area is used to calculate the activity intensity or the heartbeat state in the data processor.

The sleep information may include a plurality of sleep areas and a plurality of activity areas. In the data preprocessor, an activity area appearing after a longest sleep area among the plurality of sleep areas may be selected as the data of the activity area and an activity area appearing before the longest sleep area may be removed or ignored.

The data processor may be configured to calculate the sleep state by the following equation:

Sleep state=(length of NREM sleep period)/(recommended sleep time×0.75)

Here, the length of the NREM sleep period may be determined as a sum of sections corresponding to a low heart rate variability (HRV) in the sleep area, and the recommended sleep time may be determined based on minimum recommended sleep time data by age.

A section corresponding to the low HRV in the sleep area may be determined as a section in which a variance of heartbeat information is less than or equal to a reference variance, and the reference variance may be determined by the following equation:

$$\mu = (HR_{rest} \times 0.1)^2$$

Here, $HR_{rest}$ denotes heartbeat information about a resting heart rate and may be collected by the wearable device.

The data processor may be configured to calculate the activity intensity by the following equation:

Activity intensity=$(HR_{current}-HR_{rest})/(HR_{max}-HR_{rest})$

Here, $HR_{current}$ and $HR_{rest}$ may be collected by the wearable device, and $HR_{max}$ may be calculated by "208−0.7× user's age."

The activity intensity may be calculated at regular time intervals, and an average activity intensity in all activity areas may be calculated by the following equation:

$$\text{Average activity intensity }(\%) = \frac{1}{n}\sum_{i=1}^{n} \text{Activity intensity}_i \times 100$$

Here, n may be a number of times an activity intensity is calculated.

The data processor may be configured to calculate the heartbeat state by the following equation:

Heartbeat state=(NZ)/(BZ+NZ+TZ)

Here, NZ denotes a period of a normal heart rate.
BZ denotes a period of bradycardia.
TZ denotes a period of tachycardia.

The physical stability determination system may further include a determiner configured to determine a degree of a physical stability of the user by machine learning from the sleep state, the activity intensity or the heartbeat state calculated by the data processor.

A physical stability determination value of a user engaged in a specific occupation group may include a label. The determiner may be configured to determine the degree of the physical stability by performing semi-supervised learning based on training data including the label and training data that does not include the label.

The physical stability determination system may further include a data transmitter configured to transmit a physical stability determination value of the user determined by the determiner, and a monitoring device configured to receive the physical stability determination value of the user from the data transmitter.

According to another aspect, there is provided a physical stability determination method including collecting sleep information, activity information and heartbeat information of a user, dividing each of the activity information and the heartbeat information into data of a sleep area and data of an activity area, based on the sleep information, calculating a sleep state, an activity intensity and a heartbeat state of the user from the data of the sleep area and the data of the activity area, and determining a physical stability of the user from the sleep state, the activity intensity and the heartbeat state, wherein the data of the sleep area is used to calculate the sleep state, and the data of the activity area is used to calculate the activity intensity and the heartbeat state.

The dividing of each of the activity information and the heartbeat information may include generating an activity area appearing after a longest sleep area as the data of the activity area and removing data of an activity area appearing before the longest sleep area.

The calculating of the sleep state, the activity intensity and the heartbeat state may include calculating the sleep state by the following equation:

Sleep state=(length of NREM sleep period)/(recommended sleep time×0.75)

Here, the length of the NREM sleep period may be determined as a sum of sections corresponding to a low HRV in the sleep area, and the recommended sleep time may be determined based on minimum recommended sleep time data by age.

The calculating of the sleep state, the activity intensity and the heartbeat state may include calculating the activity intensity by the following equation:

Activity intensity=$(HR_{current}-HR_{rest})/(HR_{max}-HR_{rest})$

Here, $HR_{max}$ may be calculated by "208−0.7×user's age."

The calculating of the sleep state, the activity intensity and the heartbeat state may include calculating the heartbeat state by the following equation:

Heartbeat state=(NZ)/(BZ+NZ+TZ)

Here, NZ denotes a period of a normal heart rate.
BZ denotes a period of bradycardia.
TZ denotes a period of tachycardia.

A physical stability determination value of a user engaged in a specific occupation group may include a label. The determining of the physical stability may include determining a degree of a physical stability of the user by performing semi-supervised learning based on training data including the label and training data that does not include the label.

According to example embodiments, by a physical stability determination system and method, it is possible to determine a degree of a physical stability of a worker or laborer based on a variety of information, for example, a sleep state of the previous day, a current activity state, a resting heart rate, and the like.

According to example embodiments, by a physical stability determination system and method, it is possible to prevent loss of life and property damage due to a decrease in concentration by determining a level of difficulty of a job currently available to a worker based on a determined degree of a physical stability.

According to example embodiments, by a physical stability determination system and method, it is possible to increase a reliability of a physical stability rating through semi-supervised learning when time series data collected by a wearable device is preprocessed and processing by an equation is performed.

According to example embodiments, a physical stability determination system and method may be effectively utilized in a high-risk work situation, in particular, an occupational group that is forced to continuously work at the beginning of a work by determining a state of a worker before a work, and may predict whether a worker or trainee (who may be applicable to a variety of fields) maintains a physical stability suitable for a work, before the work is performed.

DESCRIPTION OF SPECIFIC EMBODIMENTS OF THE INVENTION

Hereinafter, example embodiments will be described with reference to the accompanying drawings. In the following description, the same elements will be designated by the same reference numerals although they are shown in different drawings. Also, in the following description of example embodiments, a detailed description of known functions and configurations incorporated herein will be omitted when it is deemed that such description will cause ambiguous interpretation of the example embodiments.

Also, to describe components according to example embodiments, the terms first, second, A, B, (a), (b), etc. may be used herein. These terms are merely used to distinguish one component from another, but not to define an essence, order or sequence of the components. It should be noted that if it is described in the specification that one component is "connected", "coupled", or "joined" to another component, a third component may be "connected," "coupled," and "joined" between the first and second components, although the first component may be directly connected, coupled or joined to the second component.

A component included in one example embodiment and a component having a common function will be described using the same names in other example embodiments. Description of one example embodiment may be applied to other example embodiments, and overlapping detailed descriptions thereof will be omitted, unless mentioned otherwise.

Figure 1:
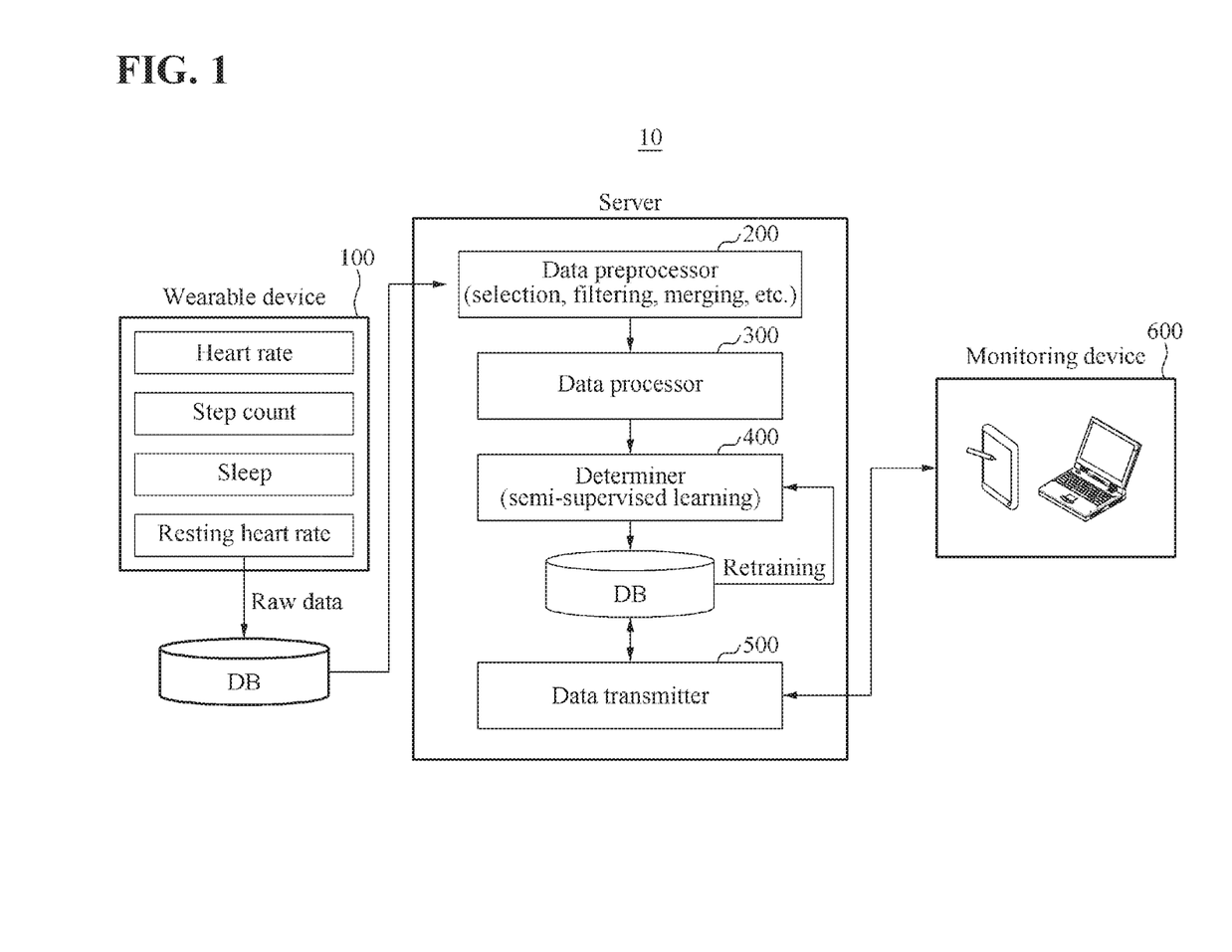
FIG. 1 illustrates a physical stability determination system according to an example embodiment.
Figure 2A:
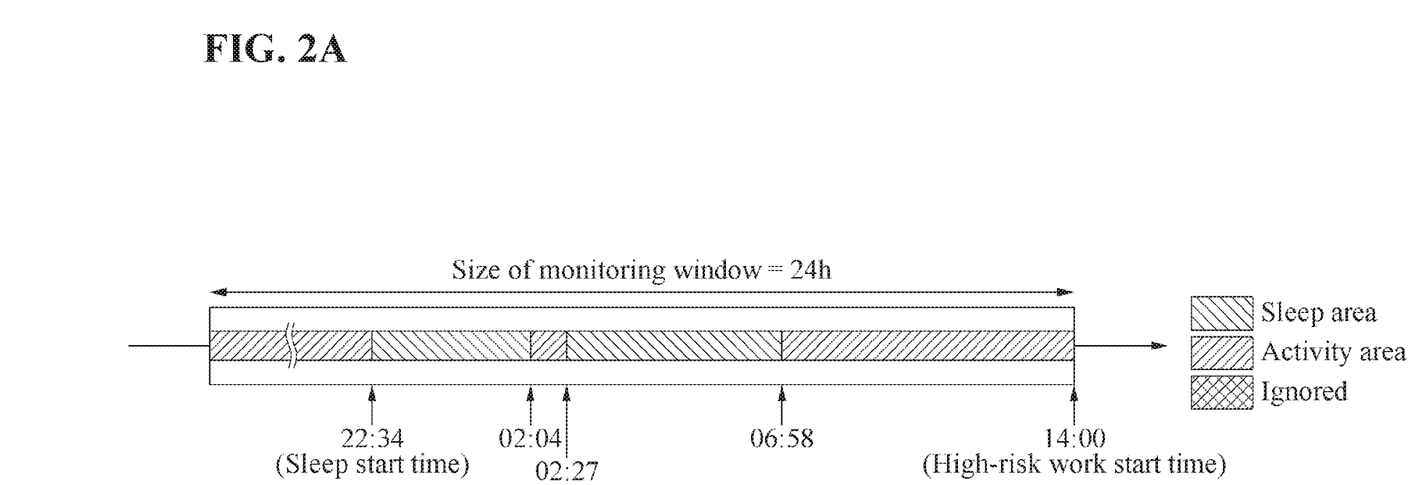
FIGS. 2A and 2B illustrate time series data in a data preprocessor.
Figure 2B:
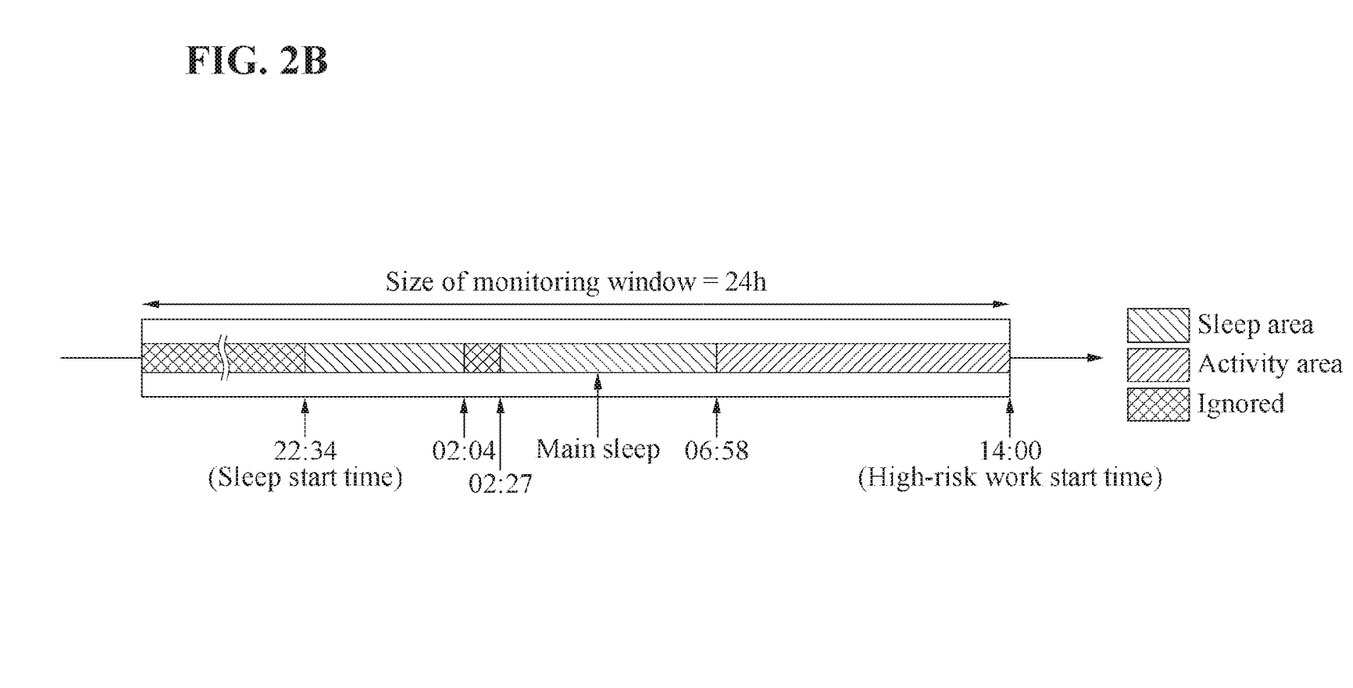
Figure 3:
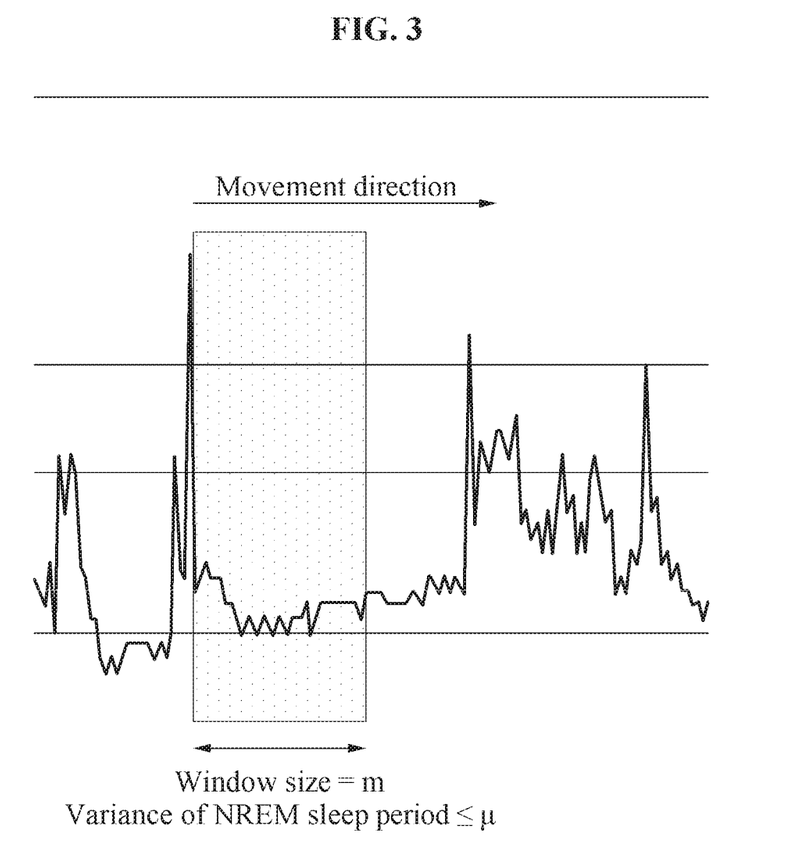
FIG. 3 illustrates a search of a non-rapid eye movement (NREM) sleep period.

FIG. 1 illustrates a physical stability determination system according to an example embodiment, FIGS. 2A and 2B illustrate time series data in a data preprocessor, and FIG. 3 illustrates a search of a non-rapid eye movement (NREM) sleep period.

Referring to FIG. 1, a physical stability determination system 10 according to an example embodiment may include a wearable device 100, a data preprocessor 200, a data processor 300, a determiner 400, a data transmitter 500 and a monitoring device 600.

The physical stability determination system 10 may broadly include the wearable device 100, a server (including the data preprocessor 200, the data processor 300, the determiner 400 and the data transmitter 500), and the monitoring device 600.

The wearable device 100 may collect sleep information, activity information or heartbeat information of a user (for example, a worker, a laborer, and the like) wearing the wearable device 100.

The sleep information, the activity information or the heartbeat information collected by the wearable device 100 may be data that may be used to determine a physical stability.

For example, the wearable device 100 may collect time series data corresponding to a number of walking steps (hereinafter, referred to as a step count), a sleep, a heart rate (HR) and a resting heart rate ($HR_{rest}$) of a user, using various sensors included in the wearable device 100.

For example, the time series data may be collected every minute.

In particular, the sleep information may indicate whether the user is currently sleeping. The sleep information may be "0" during an activity, and may be "1" during sleeping.

All the sleep information, the activity information or the heartbeat information collected by the wearable device 100 as described above may be stored in a database (DB). The DB may be included in the wearable device 100 or located outside the wearable device 100, and may be configured to communicate with the wearable device 100 via a wire or wirelessly.

The sleep information, the activity information or the heartbeat information collected by the wearable device 100 and stored in the DB as described above may be transferred to the data preprocessor 200.

For example, to determine a physical stability of the user, the sleep information, the activity information or the heartbeat information may be retrieved from the DB during 24 hours prior to beginning a hazardous work (or a work requiring high concentration). In other words, a size of a monitoring window or a window size to monitor the physical stability of the user may correspond to 24 hours.

Thus, information corresponding to the size of the monitoring window among the sleep information, the activity information and the heartbeat information collected by the wearable device 100 and stored in the DB may be transferred to the data preprocessor 200.

FIG. 2A illustrates time series data for the sleep information collected by the wearable device 100. A primary activity area may appear between 14:00 and 22:34 on the previous day, a primary sleep area may appear between 22:34 and 02:04, a secondary activity area may appear between 02:04 and 02:27, a secondary sleep area may appear between 02:27 and 06:58, and a tertiary activity area may appear between 06:58 and 14:00.

As described above, a sleep area may appear when the user is sleeping, and an activity area may appear when the user is active or not sleeping.

Each of the activity information and the heartbeat information collected by the wearable device 100 may be divided into data of a sleep area and data of an activity area, based on the sleep information collected by the wearable device 100.

Time series data of a sleep area may be used to determine a sleep state of a user in the data processor 300, and time series data of an activity area may be used to determine an activity intensity and a heartbeat state of a user in the data processor 300.

Also, time series data for the sleep information may include a plurality of sleep areas and a plurality of activity areas based on a sleep state of a user (for example, a state in which the user is woken up for a while, or a nap state).

To represent the plurality of sleep areas as one activity area, the data preprocessor 200 may preprocess the activity information and the heartbeat information of the user.

For example, all sleep areas within a monitoring window may be considered. A longest sleep area in the monitoring window may be used as a main sleep area, only an activity area appearing after the longest sleep area may be included, and an activity area appearing before the longest sleep area may not be used to determine the physical stability.

In other words, a sleep time before activity and an activity time of the day may be used to determine the physical stability, and an activity time of the previous day (an activity time before sleep) may not be used to determine the physical stability.

In particular, as shown in FIG. 2B, a primary activity area appearing between 14:00 and 22:34 and a secondary activity area appearing between 02:04 and 02:27 among the plurality of activity areas may be ignored or removed.

Thus, information collected between 14:00 and 22:34 and information collected between 02:04 and 02:27 among time series data for the activity information and the heartbeat information collected by the wearable device 100 may be ignored or removed.

The activity information and the heartbeat information collected by the wearable device 100 may be preprocessed, for example, filtered and merged, in the data preprocessor 200 based on the sleep information collected by the wearable device 100, to be suitable for determination of a physical stability.

As described above, data preprocessed in the data preprocessor 200 may be transferred to the data processor 300 to determine the physical stability.

Also, the data processor 300 may calculate a sleep state, an activity intensity, or a heartbeat state of the user based on the data preprocessed in the data preprocessor 200.

In particular, data of a sleep area, for example, activity information and heartbeat information corresponding to the sleep area, among the preprocessed data may be used to calculate or predict the sleep state of the user. Also, data of an activity area, for example, activity information and heartbeat information corresponding to the activity area, among the preprocessed data may be used to calculate or predict the activity intensity and the heartbeat state of the user.

For example, the data processor 300 may calculate the sleep state, which will be described below.

The sleep state may be represented as a percentage of user's deep sleep based on a deep sleep of a recommended sleep time using a sleep efficiency. Table 1 shows data about a minimum recommended sleep time by age.

TABLE 1

| Age | Minimum recommended sleep time |
|---|---|
| 14-17 y | 8 hours |
| 18-25 y | 7 hours |
| 26-64 y | 7 hours |
| ≥65 y | 6 hours |

Generally, a sleep cycle includes a wake period, a rapid eye movement (REM) sleep period and an NREM sleep period (stages 1, 2, 3 and 4), and only an NREM sleep stage related to a recovery of a body in the sleep cycle is used in the data processor 300. The NREM sleep stage may refer to a phase of sleep at a time during which a brain wave, for example, a δ wave, with a low oscillation frequency dominantly appears on an electroencephalogram (EEG), and may refer to a deep sleep state.

Since 25% of the total sleep time corresponds to REM sleep, a percentage of recommended NREM sleep may be calculated using the following equation:

Percentage of recommended NREM sleep=recommended sleep time×0.75

Also, since a heart rate variability (HRV) decreases in an NREM sleep period, an NREM sleep amount of a user may be calculated as a sum of sections corresponding to a low HRV in a sleep area.

A section corresponding to the low HRV in the sleep area may be determined as a section in which a variance of a heart rate measured in the wearable device 100 is less than or equal to a reference variance.

In particular, referring to FIG. 3, an NREM sleep period may be determined in a sleep area. A window of a predetermined size may be used to determine the NREM sleep period, and a section in which a variance of heartbeat information, for example, a heart rate, measured in the wearable device 100 is less than or equal to a reference variance may be determined. The reference variance may be determined by the following equation:

$$\mu = (HR_{rest} \times 0.1)^2$$

In the above equation, $HR_{rest}$ denotes heartbeat information about a resting heart rate and is included in the heartbeat information collected by the wearable device 100.

A length of an NREM sleep period (or an NREM sleep amount) among time series data of a sleep area may be used to determine the sleep state, and the sleep state may be represented as a ratio by the following equation:

Sleep state=(length of NREM sleep period)/(recommended sleep time×0.75)

As described above, the length of the NREM sleep period may be determined as a sum of sections corresponding to the low HRV in the sleep area, and a recommended sleep time may be determined based on minimum recommended sleep time data by age.

For example, when a maximum value of the sleep state is set to "100" and when a value of a sleep state calculated using the above equation exceeds "100", the value of the sleep state may be adjusted to "100".

The sleep information and the heartbeat information collected by the wearable device 100 may be utilized for the sleep state in the data processor 300, as described above. In particular, data for the heartbeat information among the data of the sleep area obtained by the dividing in the data preprocessor 200 may be utilized and calculated.

Also, the data processor 300 may calculate the activity intensity, which will be described below.

For example, the activity intensity may be calculated by inversely using the Karvonen Formula.

The Karvonen Formula based on a general momentum may be represented by the following equation:

$$HR_{recommended} = ((HR_{max} - HR_{rest}) \times \text{exercise intensity} (\%)) + HR_{rest}$$

Thus, the activity intensity may be calculated by the following equation:

$$\text{Activity intensity} = (HR_{current} - HR_{rest})/(HR_{max} - HR_{rest})$$

The activity intensity may be measured every minute.

In particular, $HR_{current}$ and $HR_{rest}$ may be collected by the wearable device 100.

$HR_{max}$ may be calculated by the following equation:

$$HR_{max} = 208 - 0.7 \times (\text{user's age})$$

For example, when a user's age is 30 years old, $HR_{max}$ may be "177."

Thus, an average activity intensity in all activity areas may be calculated by the following equation:

$$\text{Average activity intensity (\%)} = \frac{1}{n}\sum_{i=1}^{n} \text{Activity intensity}_i \times 100$$

The sleep information and the heartbeat information collected by the wearable device 100 may be utilized for the activity intensity, as described above. In particular, data for the heartbeat information among the data of the activity area obtained by the dividing and selected in the data preprocessor 200 may be utilized and calculated.

The data processor 300 may calculate the Heartbeat state, which will be described below.

The heartbeat state may be represented as a percentage of a normal heart rate in a low activity section (for example, at rest). A normal heart rate at rest for a regular adult (user) ranges from 50 (or 60) beats per minute (bpm) to 100 bpm. For example, when the normal heart rate at rest is less than 60 bpm, bradycardia may be diagnosed. When the normal heart rate at rest exceeds 100 bpm, tachycardia may be diagnosed.

Bradycardia may cause sleepiness, syncope, and the like, and tachycardia may cause dizziness, and the like, which may be dangerous during working.

The low activity section may refer to a section in which a step count less than "10" is measured after a section in which a step count less than "10" is measured for five minutes or longer. Thus, heartbeat information measured during a rest period after five minutes in which the step count is less than "10" may be utilized.

Thus, the heartbeat state (for example, a percentage of a normal heart rate ($HR_{normal}$)) may be calculated by the following equation:

$$\text{Heartbeat state} = (NZ)/(BZ + NZ + TZ)$$

In the above equation, NZ denotes a period of a normal heart rate (for example, a heart rate ranging from 50 bpm to 100 bpm).

BZ denotes a period of bradycardia (for example, a heart rate less than 50 bpm).

TZ denotes a period of tachycardia (for example, a heart rate exceeding 100 bpm).

The sleep information, the heartbeat information and the activity information collected by the wearable device 100 may be utilized for the heartbeat state, as described above. In particular, data for the heartbeat information and data for the activity information among the data of the activity area obtained by the dividing and selected in the data preprocessor 200 may be utilized and calculated.

For example, the data for the activity information among the data of the activity area may be utilized to determine a low activity section, and the data for the heartbeat information among the data of the activity area may be utilized to calculate the percentage of the normal heart rate or calculate NZ, BZ and TZ.

Also, the data processor 300 may calculate the sleep state, the activity intensity or the heartbeat state as a ratio using the equations, as described above, and thus it is possible to accurately determine an amount of user's activity, and possible to help more reliably determine a degree of a physical stability.

The sleep state, the activity intensity or the heartbeat state calculated by the data processor 300 may be transferred to the determiner 400.

The determiner 400 may determine a degree of a physical stability of a user based on the sleep state, the activity intensity and the heartbeat state calculated by the data processor 300.

The degree of the physical stability may be determined by machine learning.

The degree of the physical stability determined by the determiner 400 may include three levels, for example, excellent, good and poor.

For example, the determiner 400 may utilize the sleep state, the activity intensity or the heartbeat state calculated by the data processor 300 as training data of the machine learning. In this example, data of an activity area or sleep area with a missing value that is greater than or equal to 30% among all data may not be used as training data for an accuracy of the machine learning. The missing value may be a missing value of a heart rate, and may indicate that data corresponding to a time in which a heart rate is not measured is greater than or equal to 30% is not used as training data.

Also, to increase an accuracy of the physical stability, a label may be included in a portion of training data, or physical stability determination values of people in an occupation group, such as doctors or supervisors, who can relatively accurately determine a physical stability. However, a label may not be included in physical stability determination values of people in occupation groups other than the occupation group including doctors or supervisors.

Furthermore, data including the label and existing data that does not include the label may be used together, to perform semi-supervised learning.

When clustering is performed by the machine learning, the degree of the physical stability may be determined based on the clustering. Also, when a predetermined quantity of data is collected in the DB, the degree of the physical stability may be determined again by reperforming the semi-supervised learning.

Thus, a physical stability determination value of a user determined by the determiner 400 may be stored in the DB, or may be transmitted to the monitoring device 600 through the data transmitter 500.

For example, the data transmitter 500 may transmit data in the DB to the monitoring device 600 via a wired or wireless communication, and the monitoring device 600 may notify the user of the physical stability determination value determined by the determiner 400.

Also, recommended work information based on the physical stability determination value may be additionally generated in the determiner 400, and may be provided to the user through the monitoring device 600.

For example, when a physical stability determination value of a user corresponds to "good," recommended work information may include a "work with a low intensity". When the physical stability determination value corresponds to "excellent," the recommended work information may include a "work with a high intensity (or a work requiring high concentration)." When the physical stability determination value corresponds to "poor," the recommended work information may indicate a rest instead of a work.

The above-described physical stability determination system may determine a degree of a physical stability of a worker or laborer based on a variety of information, for example, a sleep state of the previous day, a current activity state, a resting heart rate, and the like. Also, the physical stability determination system may be effectively utilized in a high-risk work situation, in particular, an occupational group that is forced to continuously work at the beginning of a work, by determining a state of a worker before a work. In addition, the physical stability determination system may predict whether a worker or trainee (who may be applicable to a variety of fields) maintains a physical stability suitable for a work, before the work is performed.

The physical stability determination system has been described above, and a physical stability determination method according to an example embodiment will be described below.

Figure 4:
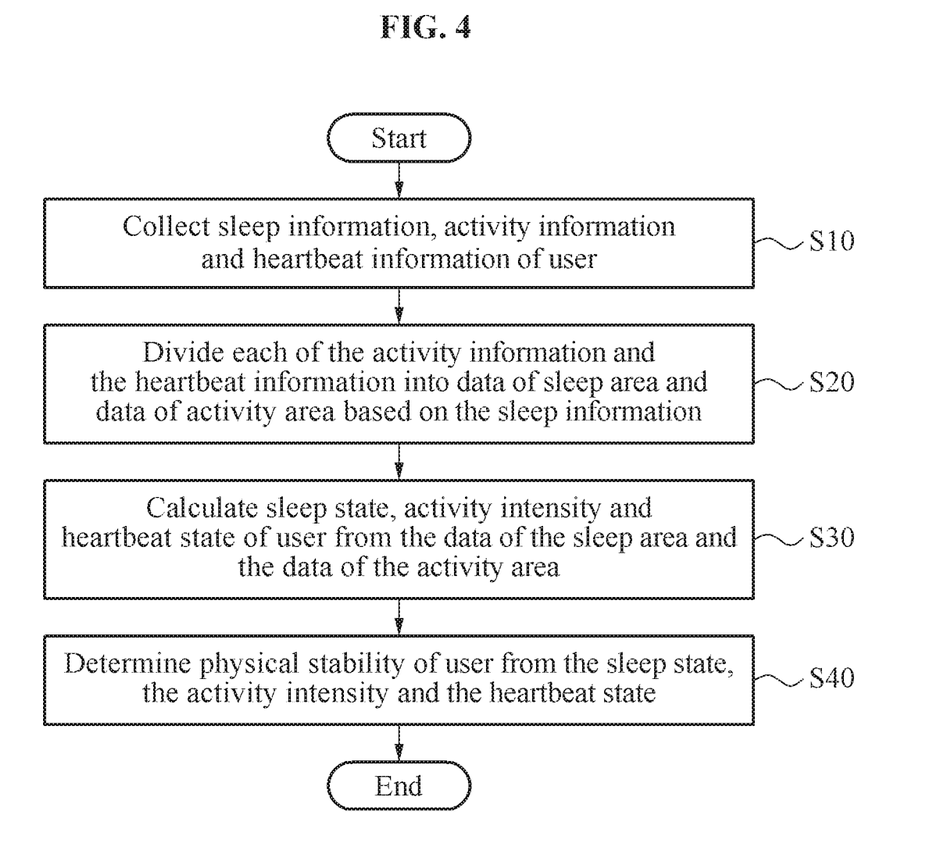
FIG. 4 is a flowchart illustrating a physical stability determination method according to an example embodiment.
Figure 5:
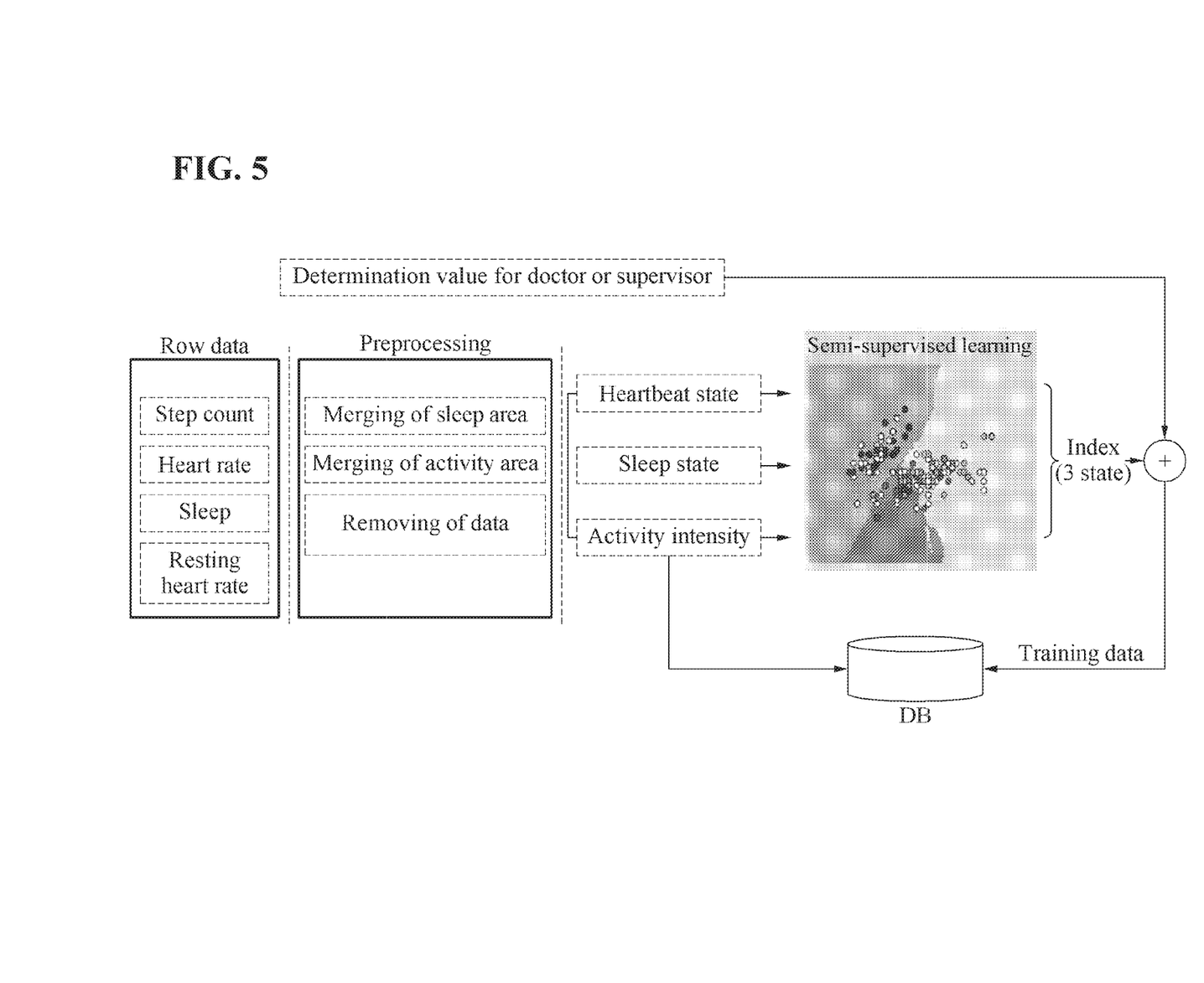
FIG. 5 illustrates a physical stability determination process according to an example embodiment.

FIG. 4 is a flowchart illustrating a physical stability determination method according to an example embodiment, and FIG. 5 illustrates a physical stability determination process according to an example embodiment.

Referring to FIG. 4 or 5, a physical stability of a user may be determined.

In operation S10, sleep information, activity information and heartbeat information of a user are collected.

For example, a user may wear a wearable device, and sleep information, activity information and heartbeat information of the user may be collected using various sensors included in the wearable device.

In operation S20, each of the activity information and the heartbeat information is divided into data of a sleep area and data of an activity area based on the sleep information.

For example, the sleep information of the user may include a plurality of sleep areas and a plurality of activity areas, and the plurality of sleep areas and the plurality of activity areas may be distinguished based on the sleep information.

In this example, to consider an activity area appearing after a longest sleep area among the plurality of sleep areas and to ignore the other activity areas, an activity area appearing before the longest sleep area among the plurality of sleep areas may be removed or ignored.

Thus, a sleep area may be merged, an activity area may be merged, and a portion of data, for example, data on the activity area appearing before the longest sleep area among the plurality of sleep areas may be removed.

Thus, the data of the sleep area, that is, activity information and heartbeat information in the sleep area may be used to calculate a sleep state of the user. The data of the activity area, that is, activity information and heartbeat information in the activity area appearing after the longest sleep area may be used to calculate an activity intensity and a heartbeat state of the user.

In operation S30, a sleep state, an activity intensity and a heartbeat state of the user are calculated from the data of the sleep area and the data of the activity area.

For example, the sleep state, such as a sleep state of the previous day, may be calculated by the following equation:

$$\text{Sleep state} = (\text{length of NREM sleep period})/(\text{recommended sleep time} \times 0.75)$$

In the above equation, the length of the NREM sleep period may be determined as a sum of sections corresponding to a low HRV in the sleep area, and the recommended sleep time may be determined based on minimum recommended sleep time data by age.

Thus, it is possible to predict a sleep state of a user based on heartbeat information corresponding to a sleep area.

Also, the activity intensity, for example, a current activity intensity of a user, may be calculated by the following equation:

Activity intensity=$(HR_{current}-HR_{rest})/(HR_{max}-HR_{rest})$

In the above equation, $HR_{max}$ may be calculated by "208−0.7×user's age."

$HR_{current}$ may refer to heartbeat information about a current heart rate of a user measured by the wearable device, and $HR_{rest}$ may refer to heartbeat information about a resting heart rate of a user measured in advance by the wearable device.

Also, the heartbeat state, for example, a percentage of a normal heart rate in a low activity section, may be calculated by the following equation:

Heartbeat state=(NZ)/(BZ+NZ+TZ)

NZ denotes a period of a normal heart rate (for example, a heart rate ranging from 50 bpm to 100 bpm).

BZ denotes a period of bradycardia (for example, a heart rate less than 50 bpm).

TZ denotes a period of tachycardia (for example, a heart rate exceeding 100 bpm).

For example, a low activity section of a user may be determined based on data for activity information among data of an activity area, and a percentage of a normal heart rate may be calculated based on data for heartbeat information among the data of the activity area.

In operation S40, a physical stability of the user is determined from the sleep state, the activity intensity and the heartbeat state that are calculated.

A degree of the physical stability may be determined by machine learning. The degree of the physical stability may include three levels, for example, excellent, good and poor. Thus, by performing the machine learning using the sleep state, the activity intensity and the heartbeat state as training data, the degree of the physical stability may be determined to be one of excellent, good and poor.

In this example, data of an activity area or sleep area with a missing value that is greater than or equal to 30% among all data may not be used as training data for an accuracy of the machine learning. The missing value may be a missing value of a heart rate, and may indicate that data corresponding to a time in which a heart rate is not measured is greater than or equal to 30% is not used as training data.

Also, to increase an accuracy of the physical stability, a label may be included in a portion of training data, or physical stability determination values of people in an occupation group, such as doctors or supervisors, who can relatively accurately determine a physical stability. However, a label may not be included in physical stability determination values of people in occupation groups other than the occupation group including doctors or supervisors.

Furthermore, data including the label and existing data that does not include the label may be used together, to perform semi-supervised learning.

By the above-described physical stability determination method, it is possible to increase a reliability of a physical stability rating through semi-supervised learning when time series data collected in a wearable device is preprocessed and processing by an equation is performed, and possible to prevent loss of life and property damage due to a decrease in concentration by determining a level of difficulty of a job currently available to a worker based on a degree of a physical stability.

While this disclosure includes specific example embodiments, it will be apparent to one of ordinary skill in the art that various changes in form and details may be made in these example embodiments without departing from the spirit and scope of the claims and their equivalents. The example embodiments described herein are to be considered in a descriptive sense only, and not for purposes of limitation. Descriptions of features or aspects in each example embodiment are to be considered as being applicable to similar features or aspects in other example embodiments. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

EXPLANATION OF REFERENCE NUMERALS

10: Physical stability determination system
100: Wearable device
200: Data preprocessor
300: Data processor
400: Determiner
500: Data transmitter
600: Monitoring device

What is claimed is:

1. A physical stability determination system comprising:
   a wearable device configured to collect sleep information, activity information and heartbeat information of a user;
   a data preprocessor configured to divide each of the activity information and the heartbeat information into data of a sleep area and data of an activity area, based on the sleep information; and
   a data processor configured to calculate a sleep state, an activity intensity or a heartbeat state of the user from the data of the sleep area and the data of the activity area,
   wherein the data of the sleep area is used to calculate the sleep state in the data processor, and the data of the activity area is used to calculate the activity intensity or the heartbeat state in the data processor.

2. The physical stability determination system of claim 1, wherein
   the sleep information comprises a plurality of sleep areas and a plurality of activity areas, and
   the data preprocessor selects an activity area appearing after a longest sleep area among the plurality of sleep areas as the data of the activity area and does not select an activity area appearing before the longest sleep area among the plurality of sleep areas as the data of the activity area.

3. The physical stability determination system of claim 1, wherein the data processor is configured to calculate the sleep state by the following equation:

Sleep state=(length of NREM sleep period)/(recommended sleep time×0.75)

and
   in which the data processor is configured to determine the length of the NREM sleep period as a sum of sections corresponding to a low heart rate variability (HRV) in the sleep area, and determine the recommended sleep time based on minimum recommended sleep time data by age.

4. The physical stability determination system of claim 3, wherein
the data processor is configured to determine a section corresponding to the low HRV in the sleep area as a section in which a variance of heartbeat information is less than or equal to a reference variance, and
the data processor is configured to determine the reference variance by the following equation:

$$\mu = (HR_{rest} \times 0.1)^2$$

in which $HR_{rest}$ denotes heartbeat information about a resting heart rate and is collected by the wearable device.

5. The physical stability determination system of claim 1, wherein the data processor is configured to calculate the activity intensity by the following equation:

$$\text{Activity intensity} = (HR_{current} - HR_{rest})/(HR_{max} - HR_{rest})$$

in which $HR_{current}$ and $HR_{rest}$ are collected by the wearable device, and the data processor is configured to calculate $HR_{max}$ by "208-0.7×user's age".

6. The physical stability determination system of claim 5, wherein
the data processor is configured to calculate the activity intensity at regular time intervals, and
the data processor is configured to calculate an average activity intensity in all activity areas by the following equation:

$$\text{Average activity intensity (\%)} = \frac{1}{n}\sum_{i=1}^{n} \text{Activity intensity}_i \times 100,$$

in which n denotes a number of times an activity intensity is calculated.

7. The physical stability determination system of claim 1, wherein the data processor is configured to calculate the heartbeat state by the following equation:

$$\text{Heartbeat state} = (NZ)/(BZ+NZ+TZ)$$

in which NZ denotes a period of a normal heart rate, BZ denotes a period of bradycardia, and TZ denotes a period of tachycardia.

8. The physical stability determination system of claim 1, further comprising:
a determiner configured to determine a degree of a physical stability of the user by machine learning from the sleep state, the activity intensity or the heartbeat state calculated by the data processor.

9. The physical stability determination system of claim 8, wherein
a physical stability determination value of a user engaged in a specific occupation group comprises a label, and
the determiner is configured to determine the degree of the physical stability by performing semi-supervised learning based on training data comprising the label and training data that does not comprise the label.

10. The physical stability determination system of claim 8, further comprising:
a data transmitter configured to transmit a physical stability determination value of the user determined by the determiner; and
a monitoring device configured to receive the physical stability determination value of the user from the data transmitter.

* * * * *